United States Patent
Satyamurthy et al.

(10) Patent No.: US 10,626,083 B2
(45) Date of Patent: Apr. 21, 2020

(54) METHODS FOR MULTI-DOSE SYNTHESIS OF [F-18]FDDNP FOR CLINICAL SETTINGS

(71) Applicant: THE REGENTS OF THE UNIVERSITY OF CALIFORNIA, Oakland, CA (US)

(72) Inventors: Nagichettiar Satyamurthy, Los Angeles, CA (US); Jie Liu, Alhambra, CA (US); Jorge R. Barrio, Agoura Hills, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 16/457,322

(22) Filed: Jun. 28, 2019

(65) Prior Publication Data
US 2019/0322616 A1    Oct. 24, 2019

Related U.S. Application Data

(62) Division of application No. 15/807,306, filed on Nov. 8, 2017, now Pat. No. 10,377,701.

(60) Provisional application No. 62/419,286, filed on Nov. 8, 2016.

(51) Int. Cl.
| | | |
|---|---|---|
| *C07C 253/30* | (2006.01) | |
| *C07C 255/34* | (2006.01) | |
| *C07C 253/34* | (2006.01) | |
| *C07B 59/00* | (2006.01) | |

(52) U.S. Cl.
CPC .......... *C07C 253/30* (2013.01); *C07B 59/001* (2013.01); *C07C 253/34* (2013.01); *C07C 255/34* (2013.01); *C07B 2200/05* (2013.01)

(58) Field of Classification Search
CPC ... C07C 253/30; C07C 253/34; C07C 255/34; C07B 59/001; C07B 2200/05
USPC ........................................................ 558/401
See application file for complete search history.

(56) References Cited

U.S. PATENT DOCUMENTS

| | | |
|---|---|---|
| 5,510,522 A | 4/1996 | Satyamurthy et al. |
| 5,861,503 A | 1/1999 | Barrio et al. |
| 6,262,254 B1 | 7/2001 | Barrio et al. |
| 6,274,119 B1 | 8/2001 | Barrio et al. |
| 6,660,530 B2 | 12/2003 | Barrio et al. |
| 7,329,401 B2 | 2/2008 | Toyokuni et al. |
| 7,341,709 B2 | 3/2008 | Barrio et al. |
| 8,372,380 B2 | 2/2013 | Barrio et al. |
| 8,674,101 B2 | 3/2014 | Satyamurthy et al. |
| 8,742,139 B2 | 6/2014 | Satyamurthy et al. |
| 8,845,999 B2 | 9/2014 | Wright et al. |
| 8,951,480 B2 | 2/2015 | Satyamurthy et al. |
| 9,211,520 B2 | 12/2015 | Satyamurthy et al. |
| 9,481,705 B2 | 11/2016 | Satyamurthy et al. |
| 2004/0072371 A1 | 4/2004 | Barrio et al. |
| 2007/0053831 A1 | 3/2007 | Barrio et al. |
| 2007/0217963 A1 | 9/2007 | Elizarov et al. |
| 2007/0218002 A1 | 9/2007 | Barrio et al. |
| 2008/0226453 A1 | 9/2008 | Nordeen et al. |
| 2010/0113763 A1* | 5/2010 | Moon .................. C07B 59/002 536/28.54 |
| 2012/0283490 A1 | 11/2012 | Gangadharmath et al. |
| 2013/0209363 A1 | 8/2013 | Berndt et al. |
| 2014/0039074 A1 | 2/2014 | Chi et al. |
| 2015/0367005 A1 | 12/2015 | Scott et al. |

FOREIGN PATENT DOCUMENTS

| | | |
|---|---|---|
| WO | 2005/040337 | 5/2005 |
| WO | 2011/095593 | 8/2011 |

OTHER PUBLICATIONS

Small, Gary W. et al., PET of Brain Amyloid and Tau in Mild Cognitive Impairment, N Engl J Med 355;25, www.nejm.org, Dec. 21, 2006, 2652-2663.
Protas, Hillary D. et al., Prediction of cognitive decline based on hemispheric cortical surface maps of FDDNP PET, NeuroImage 61 (2012) 749-760.
Braak, H. et al., Neuropathological stageing of Alzheimer-related changes, Acta Neuropathol (1991) 82: 239-259.
Folstein, Marshal F. et al., "Mini-Mental State" A Practical Method for Grading the Cognitive State of Patients for the Clinician, J. psychiat. Res., 1975, vol. 12, pp. 189-198. Pergamon Press, Printed in Great Britain.
Logan, Jean et at, Distribution Volume Ratios Without Blood Sampling from Graphical Analysis of PET Data, J Cereb Blood Flow Metab, vol. 16, No. 5, 1996, 834-840.
Wong, Koon-Pong et al., Estimation of Input Function and Kinetic Parameters Using Simulated Annealing: Application in a Flow Model, IEEE Transactions on Nuclear Science, vol. 49, No. 3, Jun. 2002, 707-713.
Heap, B.R., Permutations by interchanges, undated, (2pages), 1963.
Barrio, Jorge R. et al., In vivo characterization of chronic traumatic encephalopathy using [F-18]FDDNP PET brain Imaging, PNAS, Published online Apr. 6, 2015, E2039-E2047.

(Continued)

*Primary Examiner* — Kristin A Vajda
(74) *Attorney, Agent, or Firm* — Vista IP Law Group LLP

(57) ABSTRACT

A method of manufacturing 2-(1-{6-[(2-[F-18]fluoroethyl)(methyl)amino]-2-naphthyl}ethylidene)-malononitrile ([F-18]FDDNP) utilizes a semi-automated module that is used to perform fluorination, pre-purification, separation, product extraction, and formulation. The method is able to produce [F-18]FDDNP with high yields and ready for human administration under existing FDA regulations, and without the need for hazardous organic solvents such as dichloromethane (DCM), methanol (MeOH), and tetrahydrofuran (THF). The method also improves the speed with which [F-18] FDDNP can be synthesized with the method being able to generate a final product within about 90 to 100 minutes. This synthesis method is easily adaptable to FDA registered and approved automated synthesis systems.

14 Claims, 5 Drawing Sheets

(56) References Cited

OTHER PUBLICATIONS

Faul, Mark et al., Traumatic Brain Injury in the United States, Emergency Department Visits, Hospitalizations and Deaths 2002-2006, U.S. Department of Health and Human Services Centers for Disease Control and Prevention, www.cdc.gov/TraumaticBrainInjury (74pages).
Grossberg, George T. et al., The Art of Sharing the Diagnosis and Management of Alzheimer's Disease with Patients and Caregivers: Recommendations of an Expert Consensus Panel, Prim Care Companion J Clin Psychiatry; 2010; 12(1); PCC.09cs00833.
Beard, John R. et al., The World report on ageing and health: a policy framework for healthy ageing, www.thelancet.com, vol. 387, May 21, 2016, 2145-2154.
Langlois, Jean A. et al., The Epidemiology and Impact of Traumatic Brain Injury, J Head Trauma Rehabil, vol. 21, No. 5, pp. 375-378 (2006).
Liu, Jie et al., High-Yield, Automated Radiosynthesis of 2-(1-{6-[(2-[18F]Fluoroethyl)(methyl)amino]-2-napthyl}ethylidene)malononitrile([18F]FDDNP) Ready for Animal or Human Administration, Mol Imaging Biol (2007) 9:6-16. DOI: 10.1007/s11307-006-0061-4.
Okie, Suan, Traumatic Brain Injury in the War Zone, N Engl J Med 352;20, www.nejm.org, May 19, 2005, 2043-2047.
Tauber, Clovis et al., Brain [18F]FDDNP Binding and Glucose Metabolism in Advanced Elderly Healthy Subjects and Alzheimer's Disease Patients, Journal of Alzheimer's Disease, 36 (2013) 311-320.
Thompason, Paul M. et al., Detection and Mapping of Abnormal Brain Structure with a Probabilistic Atlas of Cortical Surfaces, Journal of Computer Assisted Tomography, vol. 21(4), Jul./Aug. 1997, pp. 567-581.
Wong, K. et al., A novel data-driven approach to order subjects with neurodegenerative disease based on PET imaging data alone, Supplement to the Journal of Nuclear Medicine, The Official Publication of SNMMI, SNMMI 2015 Annual Meeting Scientific Abstracts Search 2015 Annual Meeting abstracts online starting May 15, 2015 (http://jnm.snmjournals.org), JNM, vol. 56, Supplement 3, May 2015.
Wong, Koon-Pong et al., A semi-automated workflow solution for multimodal neuroimaging: application to patients with traumatic brain injury, Brain Informatics (2016) 3:1-15. DOI 10.1007/s40708-015-0026-y.
Croes, G. A., A Method for Solving Traveling-Salesman Problems, Operations Research, Nov.-Dec. 1958, 791-812.
Della Croce, Federico, Generalized pairwise interchanges and machine scheduling, European Journal of Operational Research, 83 (1995) 310-319.
Wong, Koon-Pong et al., Simplified quantification of FDDNP PET studies, J Nucl Med, May 2011, vol. 52, No. supplement 1, 104.
Durstenfeld, Richard, Algorithms, Communications of the ACM, vol. 7, No. 7, Jul. 1964.
Wong, Koon-Pong, A Novel Data-Driven Approach to Order Subjects with Neurodegenrative Disease Based on PET Imaging Data Alone, UCLA, Departments of Molecular and Mediacal Pharmacology, Psychiatry and Biobehavioral Sciences, and Biomathematics, David Geffen School of Medicine at UCLA, Los Angeles, California, undated, undated, (1page), 2015.
Q3C—Tables and List Guidance for Industry, U.S. Department of Health and Human Services Food and Drug Administration, Center for Drug Evaluation and Research (CDER), Center for Biologics Evaluation and Research (CBER), Jun. 2017, ICH, Revision 3 (10pages).
PCT International Search Report for PCT/US2017/060637, Applicant: The Regents of the University of California, Form PCT/ISA/210 and 220, dated Jan. 4, 2018 (4pages).
PCT Written Opinion of the International Search Authority for PCT/US2017/060637, Applicant: The Regents of the University of California, Form PCT/ISA/237, dated Jan. 4, 2018 (6pages).
PCT International Preliminary Report on Patentability (Chapter I of the Patent Cooperation Treaty) for PCT/US2017/060637, Applicant: The Regents of the University of California, Form PCT/IB/326 and 373, dated May 23, 2019 (8pages).

\* cited by examiner

METHODS FOR MULTI-DOSE SYNTHESIS OF [F-18]FDDNP FOR CLINICAL SETTINGS

RELATED APPLICATION

This Application is a divisional Application of U.S. patent application Ser. No. 15/807,306, filed on Nov. 8, 2017, now issued as U.S. Pat. No. 10,377,701, which also claims priority to U.S. Provisional Patent Application No. 62/419,286 filed on Nov. 8, 2016, which is hereby incorporated by reference in its entirety. Priority is claimed pursuant to 35 U.S.C. § 119 and any other applicable statute.

TECHNICAL FIELD

The technical field generally relates to a method of synthesizing 2-(1-{6-[(2-[F-18]fluoroethyl)(methyl)amino]-2-naphthyl}ethylene)-malononitrile ([F-18]FDDNP) using a semi-automated synthesis module. The method is used to synthesize [F-18]FDDNP with high yields and short production times, ready for human administration. The method also introduces a non-aqueous workup procedure and does not use a combination of hazardous organic solvents that have been used in prior synthesis operations.

BACKGROUND 2-(1-{6-[(2-[F-18]fluoroethyl)(methyl)amino]-2-naphthyl}ethylidene)-malononitrile ([F-18]FDDNP) PET imaging has been used for classifying and staging progressive diseases, like Alzheimer's disease (AD) and Chronic Traumatic Encephalopathy (CTE). Almost two decades of clinical research experience in the U.S., Europe, and Asia has demonstrated the ability of [F-18]FDDNP to differentiate Alzheimer's disease (AD) from normal aging, mild cognitive impairment, and several other neurodegenerative diseases (e.g., progressive supranuclear palsy, dementia with Lewy bodies, Down syndrome). The ability of [F-18]FDDNP to differentiate AD from normal aging is comparable to that of 2-deoxy-2-[F-18]fluoro-D-glucose ([F-18]FDG). Moreover recent clinical research demonstrates a distinct [F-18]FDDNP binding pattern in retired athletes and military personnel with a history of traumatic brain injury and suspected CTE, and this pattern can be readily differentiated from that of AD. Currently there is no available biomarker that can detect suspected CTE in living people at risk, and other PET ligands for this purpose are very early in their development.

Liu et al. discloses one method for the automated radiosynthesis of [F-18]FDDNP. See Liu, J. et al., High-yield, automated radiosynthesis of 2-(1-{6-[(2-[$^{18}$F]fluoroethyl)(methyl)amino]-2-naphthyl}ethylidene-malononitrile([$^{18}$F]FDDNP) ready for animal or human administration, Mol. Imaging Biol., 9: 6-16 (2007). However, this previously reported synthesis of [F-18]FDDNP for the preparation of multi-dose quantities of tracer has certain limitations. First, this method uses a rather complex pre-purification of the F-18 fluorination reaction mixture using cumbersome multiple cartridges and evaporation processes prior to semi-preparative HPLC purification. Second, it uses toxic and potentially harmful organic solvents in the pre-purification and semi-preparative HPLC purification steps (e.g., dichloromethane, methanol (MeOH), and tetrahydrofuran). Third, autoradiolytic decomposition of [F-18]FDDNP could potentially occur during the pre-purification and HPLC purification processes. Autoradiolytic decomposition can generally be a serious issue with F-18 labeled compounds with high specific activities leading to a reduction in radiochemical yields, decreased product stability, and increase in radiochemical impurities. In the previously reported synthesis, the formulation and sterilization of the product in human serum albumin (HSA) also lowers the radiochemical yield of the final product to about 27%. Radiochemical yields are particularly important because positron emitter labeled biomarkers like [F-18]FDDNP have a relatively short half-life (half-life of F-18 isotope is 110 minutes).

Two considerations are important for the use of these biomarkers in clinical settings, which is the primary intent for the use of [F-18]FDDNP to characterize CTE and AD, among other neurodegenerative diseases. First, such biomarkers or probes are often produced in one geographic location (e.g., where a cyclotron is located), but used in remote geographic regions. Transportation of F-18 labeled biomarkers over relatively longer geographical distances will invariably result in lower final usable doses. It is thus critically important to achieve as high a radiochemical yield as possible so that one batch of [F-18]FDDNP can be divided into multiple doses that can efficiently be used even in geographically remote locations. Second, in U.S. Food and Drug Administration (FDA)-sponsored clinical trials and clinical use of PET biomarkers, the easiness, reproducibility and reliability of the final product ready for injection are essential.

SUMMARY

A modular method for the synthesis of [F-18]FDDNP is disclosed for clinical settings. This approach is highly reliable and can produce up to one hundred (100) 10 mCi batch doses of pure, high specific activity (typically from 1 to 5 Ci/micromole) [F-18]FDDNP biomarker ready for human injection using available biomedical cyclotrons routinely producing up to 5-10 Ci of [F-18]fluoride ion. Product preparation by trained technicians using this method is thus easily achievable, an important condition in high throughput clinical settings. Alternatively, the synthesis method may be implemented in an automated radiosynthesizer. The method reduces synthesis time, significantly simplifies the synthesis procedure, most specifically the complex pre-purification of the F-18 fluorination reaction mixture using cumbersome multiple cartridges and organic solvents, and evaporation processes prior to semi-preparative HPLC purification. Among others, a critical improvement made in the method includes utilization of an alumina-based cartridge for the purification of the crude radioactive reaction mixture and inclusion of ascorbic acid in the semi-preparative HPLC mobile phase. A main purpose of the synthesis procedure disclosed herein is to have a high throughput chemical synthesis, a reliable chemical method which essentially covers two purposes: (1) a high yield synthesis, which would permit transportation of a pure, final product to relatively distant sites to compensate for product decay (at least to some extent) due to the short half-life of the F-18 isotope (half-life: 110 min); and (2) the ease of synthesis will permit easy adaptation of this synthesis to any FDA-approved automated radiosynthesizer (or manual/semi-automated synthesis setups) at any sites having cyclotrons. Thus, the utilization of this PET probe could be greatly facilitated at multiple clinical sites. The synthesis method for [F-18]FDDNP disclosed herein is easily adaptable to most FDA-approved automatic synthesis devices for PET biomarkers.

The use of the alumina cartridge was found to be superior to the incommodious multiple cartridge system previously utilized in the initial purification of the F-18 fluorinated reaction mixture. In the method used herein, a single alumina cartridge efficiently removes, in a single step, inorganic materials (e.g., $K_2CO_3$) and cryptands (e.g., Kryptofix®), as well as some of the organic side products formed during the F-18 fluorination reaction, while causing less decomposition. The inclusion of ascorbic acid in the semi-preparative HPLC mobile phase had a beneficial effect particularly when using aqueous acetonitrile in the purification process. For example, ascorbic acid prevented the autoradiolytic decomposition of [F-18]FDDNP during the HPLC purification process.

In one embodiment, no-carrier-added [F-18]fluoride ion was produced by 11 MeV proton bombardment of 90-98% enriched [O-18]water. The aqueous [F-18]fluoride ion was trapped on an anion resin cartridge to recover the [O-18] water. The [F-18]fluoride ion was subsequently released by passing 0.25% (weight:volume basis) aqueous solution (0.4 mL) of a potassium salt (e.g., $K_2CO_3$) into a glass reaction vessel pre-loaded with 4,7,13,16,21,24-Hexaoxa-1,10-diazabicyclo[8.8.8]hexacosane cryptand (e.g., Kryptofix® 2.2.2.) (10 mg) dissolved in 1.0 mL of acetonitrile. The solution was evaporated at 115° C. with a stream of nitrogen gas bubbling into it. The residue was dried by the azeotropic distillation with acetonitrile (3×0.5 mL). To the dry residue, a solution of the tosyloxy precursor 2-{[6-(2,2-dicyano-1-methylvinyl)-2-naphthyl](methyl)amino}ethyl-4-methyl-benzenesulfonate (DDNPTs) (2.2-2.5 mg) in acetonitrile (0.7 mL) was added and the reaction mixture was heated at 93° C. for 15 min. The solution was cooled with a nitrogen stream for 1 min. The mixture was then passed through a neutral alumina-containing cartridge (e.g., Sep-Pak® Light), which was pre-rinsed with anhydrous MeCN (6 mL). More anhydrous MeCN (2×0.5 mL) was used to rinse the reaction vessel and the alumina-containing cartridge. The collected MeCN eluent was diluted with ice-cold aqueous solution of 0.1 M ammonium acetate ($NH_4OAc$) and 0.02 M ascorbic acid (1.5 mL), then injected into semi-preparative HPLC column (Waters Symmetry, PrepC18 7µ, 7.8×300 mm). The HPLC column was eluted with 50% MeCN in an aqueous solution of 0.1 M $NH_4OAc$ and 0.02 M ascorbic acid at a flow rate of 5.0 mL/min. The effluent from the HPLC column was monitored with a UV detector ($\lambda$=440 nm) followed by a gamma radioactive detector. The HPLC fraction containing chemically and radiochemically pure [F-18]FDDNP product that eluted with a retention time of ~21 min was collected for 1.25 min. The collected HPLC fraction was diluted with water (9 mL) then passed through a solid-phase extraction cartridge (e.g., tC18 1 cc vac Sep-Pak® (50 mg)). The extraction cartridge was washed with sterile water (20 mL). The [F-18]FDDNP was then eluted off the solid-phase extraction cartridge with ethanol (EtOH (0.5 mL)) into a glass vessel and mixed with saline (total 5.5 mL) and 25% human serum albumin (total 4 mL). The pure [F-18]FDDNP product in EtOH/saline/human serum albumin was sterilized by passing through a Millex® GV filter (0.22 µm) and collected in a sterile multi-dose vial.

In one embodiment, a method of manufacturing 2-(1-{6-[(2-[F-18]fluoroethyl)(methyl)amino]-2-naphthyl}ethylidene)-malononitrile ([F-18]FDDNP) includes trapping [F-18]fluoride ion from a [F-18]fluoride ion-containing solution in a resin cartridge. The [F-18]fluoride ion is then eluted into a reaction vessel having a cryptand solution contained therein by passing a potassium salt solution (e.g., $K_2CO_3$). The [F-18]fluoride/cryptand complex thus formed is subjected to multiple rounds of azeotropic evaporation with anhydrous acetonitrile to form dried [F-18]fluoride ion/cryptand complex residue in the reaction vessel. The dried [F-18]fluoride ion/cryptand complex is reacted with tosyloxy precursor 2-{[6-(2,2-dicyano-1-methylvinyl)-2-naphthyl](methyl)amino}ethyl-4-methyl-benzenesulfonate (DDNPTs) in anhydrous acetonitrile to form a reaction product. The reaction product is then passed or flowed through an alumina cartridge and into an injection vessel. The reaction product contained in the injection vessel is diluted with an ice-cooled $NH_4OAc$/L-ascorbic acid solution and then passed or flowed to an HPLC column. A fraction containing [F-18]FDDNP is collected from the HPLC column in a dilution vessel. The collected [F-18] FDDNP contained in the dilution vessel is then diluted with water and passed or flowed through a solid-phase extraction cartridge followed by elution of the [F-18]FDDNP with ethanol. The eluted [F-18]FDDNP (with ethanol) is then diluted with saline and human serum albumin to form a final product (i.e., formulation).

The method is used to synthesize [F-18]FDDNP ready for human administration with high yields and short production times. The method also does not use a combination of hazardous organic solvents that have been used in prior synthesis operations. For example, there is no methanol, dichloromethane, or tetrahydrofuran in the final product. To the extent that the final product contains trace amounts of acetonitrile, the amount is well below FDA guideline levels.

DETAILED DESCRIPTION OF ILLUSTRATED EMBODIMENTS

Figure 1:
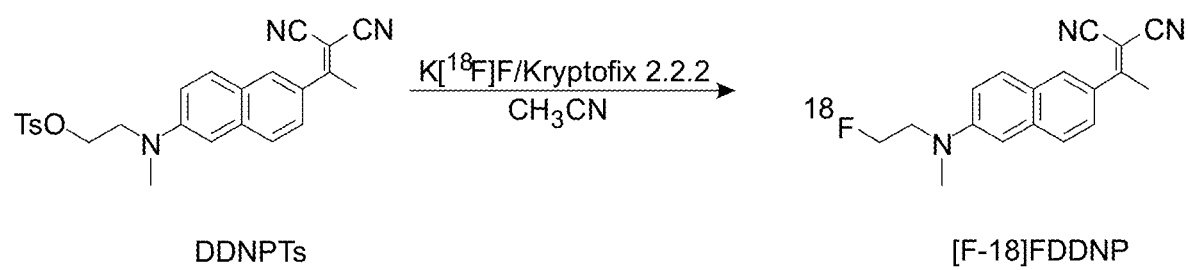
FIG. 1 schematically illustrates the reaction that is used to produce [F-18]FDDNP.
Figure 2A:
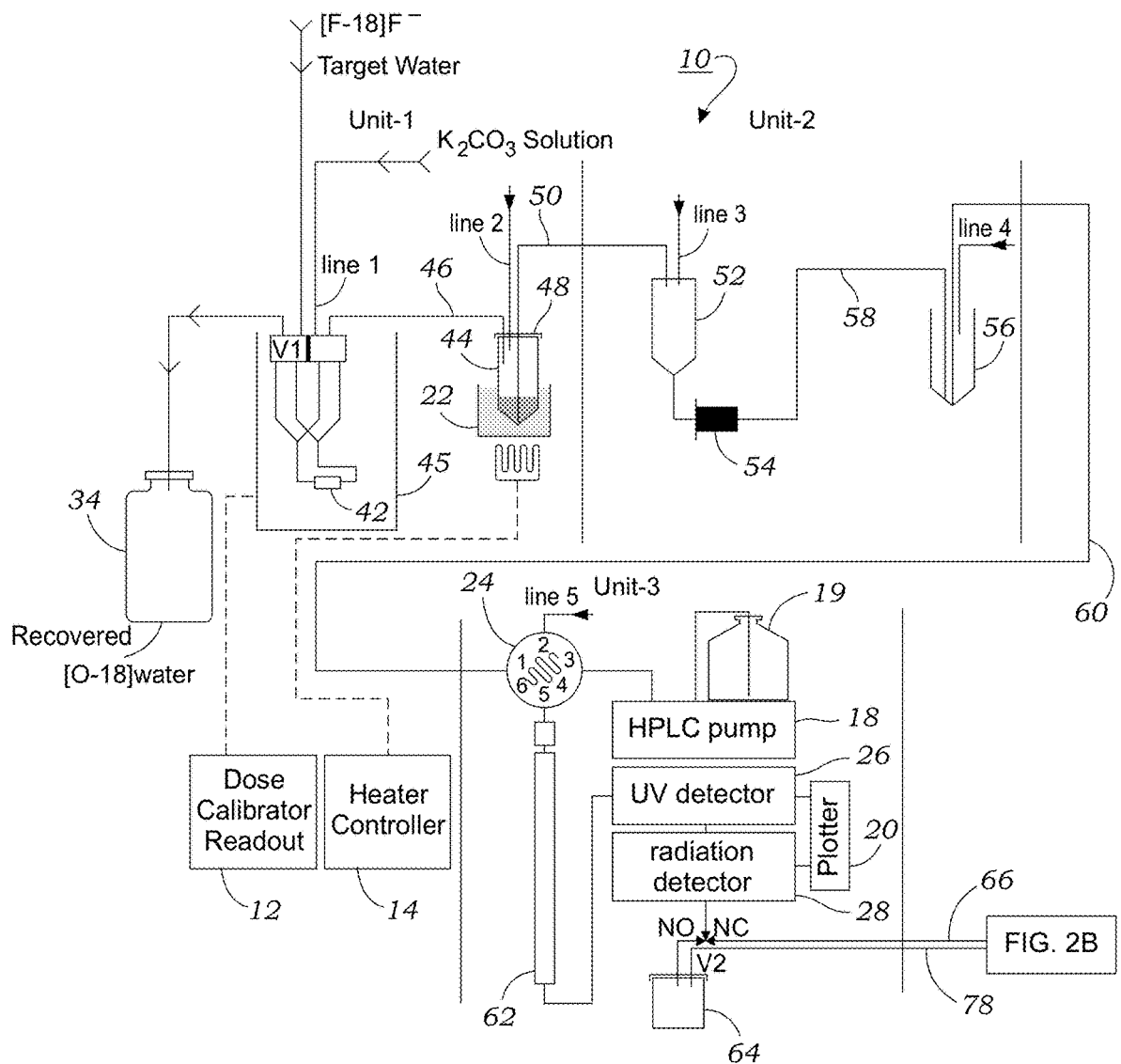
FIGS. 2A-2B illustrate a schematic diagram of the semi-automated synthesis module used for the synthesis of [F-18] FDDNP; including unit operations performed by various components of the module.
Figure 2B:
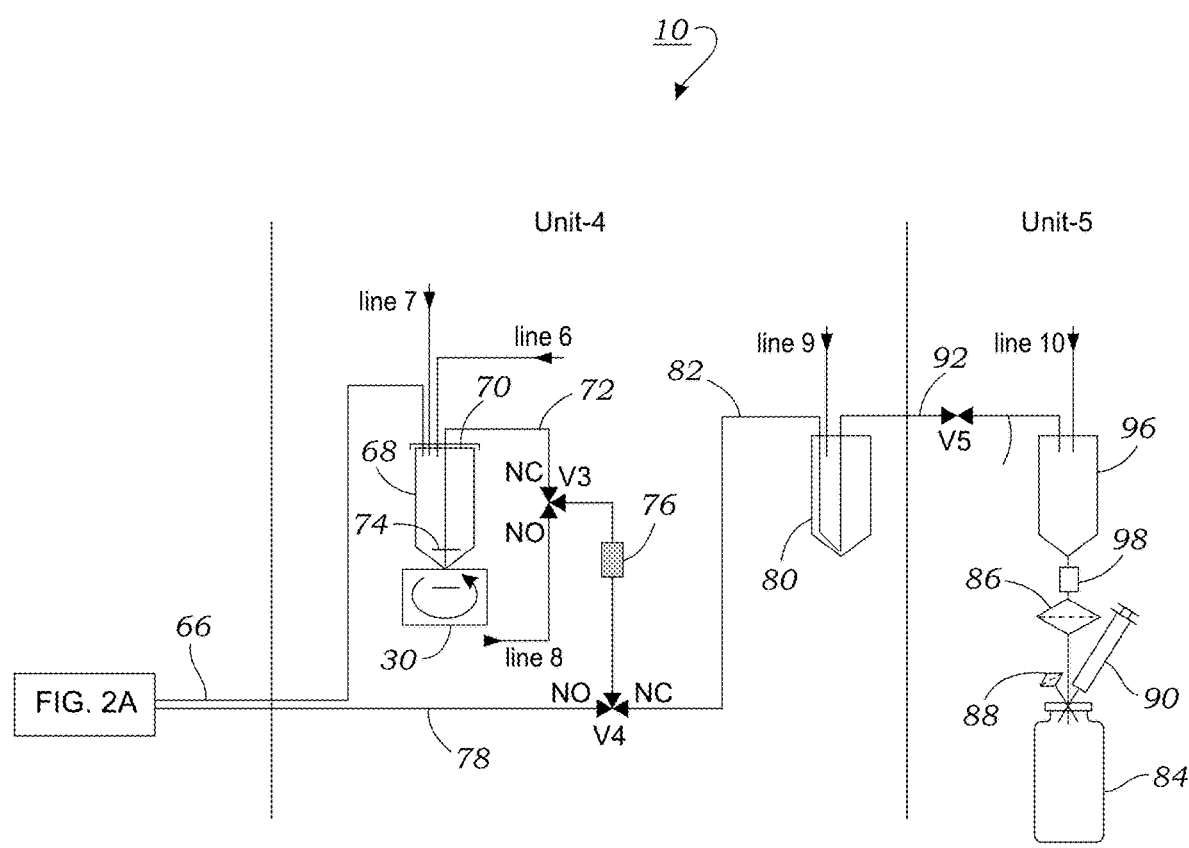

FIG. 1 illustrates the radiochemical reaction that leads to the production of the biomarker or PET tracer 2-(1-{6-[(2-[F-18]Fluoroethyl)(methyl)amino]-2-naphthyl}ethylidene) malononitrile ([F-18]FDDNP) from the tosyloxy precursor 2-{[6-(2,2-dicyano-1-methylvinyl)-2-naphthyl](methyl) amino}ethyl-4-methylbenzenesulfonate (DDNPTs). Subsequent to preparation or synthesis, the PET tracer [F-18] FDDNP is purified by semi-preparative High Performance Liquid Chromatography (HPLC). FIGS. 2A-2B illustrate a schematic diagram of the semi-automated module 10 used for the preparation of [F-18]FDDNP. The semi-automated module 10 is setup in a "hot cell" that is found in a cyclotron or other radiochemistry laboratory. The hot cell is a dedicated enclosure that is used for the handling of radioactive materials. The hot cell is exhausted and radiation shielded enclosures that prevent the technician or operator from exposure to radiation from gamma ray emitters. Various types of concrete, lead, lead glass, steel, and depleted uranium can be used for shielding materials.

As explained herein, some components of the semi-automated module 10 may be located outside the hot cell. These may include the dose calibrator readout 12, heater controller 14, HPLC pump 18, HPLC solvent reservoir 19, and strip chart recorder or plotter 20, as well as input lines or tubing that are used to delivery various reagents and solvents to the module 10. The heating bath 22, valves (V1-V5), HPLC injector 24, detectors 26, 28, stirring machine 30 are remotely controlled via power switches (not illustrated) located outside the hot cell.

As seen in FIGS. 2A-2B, the semi-automated module 10 has five (5) functional units (i.e., identified as UNITS 1-5), with each unit performing one of the five steps of the radiosynthesis (fluorination, pre-purification, separation, product extraction, formulation). It should be appreciated that UNITS 1-5 are not physically separate units; a single semi-automated module 10 is used for the synthesis. The UNITS 1-5 that are described herein are referred to as individual units that each performs different operations or processes in the synthesis and final formulation yet are part of a single overall module 10. The individual components of the units are connected to one another via tubing or lines (e.g., Polytetrafluoroethylene (PTFE) or Teflon® tubing) and the terminals of the tubing may be fitted with male or female Luer tips for connection with stopcocks/syringes. During the operation, reagents and solvents are added to the system remotely via tubing or lines (e.g., Line 1-Line 10 as seen in FIGS. 2A and 2B) by application of either vacuum or positive pressure from outside of the hot cell, using a 60 mL syringe, nitrogen gas (for applying positive pressure), or other source of vacuum.

Described below are the individual units and their construction and function.

UNIT-1 Fluorination unit: This unit includes an automated pinch valve (V1) with a loop or flow path that is used for delivering [F-18]fluoride ion to a resin cartridge 42 for subsequent elution. In one embodiment, the resin cartridge 42 is an anion exchange resin cartridge that is prepared to isolate [F-18]fluoride ion from proton irradiated [O-18] water in order to conserve the [O-18]water and reduce the amount of water that needs to be evaporated during the synthesis. In one embodiment the resin cartridge 42 is custom made by loading 0.125 inch (inner diameter), 0.160 inch (outer diameter) PTFE tubing with BioRad® MP-1 resin (catalog #1411851 available from BioRad®, Hercules, Calif.). The BioRad® MP-1 resin is a macroporous strong anion exchange resin that uses a matrix of styrene divinylbenzene. The functional group is R—CH$_2$N$^+$(CH$_3$)$_3$. The BioRad® MP-1 resin is packed into the tubing using either gravity settling or pulling the resin in the tube with vacuum. The resin is retained in the tubing using a pair of frits (made from 70 μm pore polyethylene frit material) that are formed with a ⅛ inch hole punch. The frits secure the resin material inside the tube and permit the passage of fluid through the resin material. The ends of the tubing may be fitted with Luer fittings to finalize the formation of the resin cartridge 42.

When V1 is off (normally open), the valve V1 pinches or closes the flow path on the right side of the valve V1 in FIG. 2A and allows the target water to flow through resin cartridge 42 (also referred to as cartridge MP-1) where the [F-18]fluoride ion is loaded onto the resin contained in the resin cartridge 42 while the [O-18]water proceeds to the collection vial 34. When V1 is on, the valve V1 pinches or closes the flow path on the left side of the valve V1, whereby a potassium carbonate (or other potassium salt) solution can be flowed through the resin cartridge 42 to elute the [F-18] fluoride ion to the reaction vessel 44.

The anion exchange resin cartridge 42 (e.g., MP-1 cartridge) that is located in the flow loop associated with valve V1 is for trapping [F-18]fluoride ion from the cyclotron irradiated target water. The cartridge 42 traps [F-18]fluoride ion and lets the [O-18]water pass through in order to be recovered in a 30 mL glass vial 34. A dose calibrator 45 (Model CRC-15R, Capintec, Inc., Florham, N.J.) is used for measuring the radioactivity trapped in the resin cartridge 42. The dose calibrator 45 is a well that is located in the hot cell and holds the valve V1 and the resin cartridge 42. The radioactivity is read by pressing the F-18 key on the instrument readout unit 12 that is coupled the dose calibrator sensor 45. The [F-18]fluoride ion that is trapped on the resin cartridge 42 is released by the addition of 0.4 mL of 0.25% potassium carbonate solution in water (other potassium salts may also be used), which is added via line 1 (made from PTFE), and collected in the fluorination reaction vessel 44 via the delivery line 46 (also made from PTFE). A heating oil bath 22 sits on a motorized jack platform (not shown) that permits the bath to selectively contact with reaction vessel 44. The glass fluorination reaction vessel 44 is positioned above the bath 22 with a silicon stopper 48 carrying three PTFE tubes (tube 46, line 2, and tube 50) to the reaction vessel 44. Line 2 is used for the addition of acetonitrile for the azeotropic drying of the aqueous [F-18]fluoride ion. Line 2 is also used to add the cryptand solution (e.g., Kryptofix®/MeCN solution) as well as the precursor reagent that contains DDNPTs to the reaction vessel 44 that contains the dried [F-18]fluoride ion/cryptand complex residue. During the evaporation of acetonitrile from the fluorination reaction vessel 44, a gentle gas bubbling is enabled by connecting a source of nitrogen to the PTFE line 3 in UNIT 2 which transfers nitrogen via tube 50.

UNIT-2 Alumina Sep-Pak® pre-purification unit: The fluorination reaction mixture from UNIT-1 is transferred to a glass syringe barrel 52 (3 mL) coupled to an alumina-containing cartridge 54 (Sep-Pak® Alumina N Plus Light Cartridge, product number WAT023561 Waters Corporation, Milford Mass.) by applying vacuum through line 3 which draws the reaction mixture from reaction vessel 44 to the glass syringe barrel 52 via PTFE tube 50. The alumina cartridge 54 is connected to the HPLC injection vessel 56 via PTFE tubing 58. Fluid passage through the alumina cartridge 54 is achieved by application of positive pressure (e.g., of nitrogen) through line 3 into glass syringe barrel 52.

UNIT-3 Semi-preparative HPLC unit: The crude product mixture in the injection vessel 56 is then transferred to an electrically actuated HPLC injector valve 24 via line or tubing 60 that has a 3 mL loop volume by applying vacuum through a connected PTFE line (e.g., line 5). PTFE Line 4 is used for adding aqueous solution to the HPLC injection vessel 56 as seen in UNIT-2. Upon injection of the crude reaction mixture into the HPLC column 62 (Waters Symmetry PrepC18, 7μ, 7.8×300 mm) using HPLC valve 24, the column effluent passes through an UV detector 26 followed by a gamma radioactivity detector 28. The detector signals are recorded with a strip chart recorder 20. The three-way solenoid valve V2 permits one to divert HPLC eluent to either waste 64 or to a collect position whereby the eluent enters tubing 66 for transfer to UNIT-4 (seen in FIG. 2B). Note that for valves V2, V3, and V4, "NO" stands for normally open. NC stands for normally closed.

UNIT-4 Product extraction unit: The HPLC fraction from UNIT-3 is received in a glass dilution vessel 68 via tubing 66 and is capped with a septum 70 carrying multiple lines. PTFE line 6 is used for dilution of the HPLC fraction with water, a transfer line 72 is used to siphon the content of the vessel 68 through a three-way solenoid valve V3, and line 7 acts as a vent line. The contents of the dilution vessel 68 are magnetically stirred with stirring device 30 and a magnetic stir-bar 74. The stir-bar 74 is placed in the dilution vessel 68 in advance of the preparation to homogenize the liquids contained therein. A cartridge 76 containing a silica-based bonded phase with strong hydrophobicity (Sep-Pak® tC18 1 cc Vac Cartridge, product number WAT0549 Waters Corporation, Milford Mass.) is connected to an output of solenoid valve V3. The contents of dilution vessel 68 are flushed through the cartridge 76 by applying pressure through line 6 (while line 7 is capped) to trap the drug substance on the cartridge 76 while solvents end up in a waste vial 64 through a three-way solenoid valve V4 via line 78. When the cartridge 76 is rinsed with water via a PTFE tubing line 8, the rinsing also ends up in the waste vial 64. When the radioactive product trapped in the cartridge 76 is released with the addition of ethanol (also input from PTFE tubing line 8), the product passes through the solenoid valve V4 and is collected in a mixing vessel 80 via tubing or line 82. The product in ethanol in the mixing vessel 80 is then diluted with normal saline (total 5.5 mL) and human serum albumin (HSA) (total 4.0 mL) added via PTFE line 9.

UNIT-5 Final drug sterilization unit: The final drug product vial 84 is coupled to a 25 mm sterile filter 86 (for sterilization of the product solution) and a 4 mm sterile filter 88 (for vent) and a sterile needle/sterile syringe 90 is assembled in advance under aseptic conditions in a laminar flow hood. The contents of the mixing vessel 80 from UNIT-4 are transferred through a two-way solenoid valve V5 via line 92 to a glass syringe barrel 96 (10 mL) by applying vacuum through a connected PTFE line 10. After transfer, application of positive pressure through line 10 pushes the product through a check valve 98 and the sterilizing filter 86 into the sterile final drug product vial 84.

In order to setup the semi-automated reaction module the following operations are performed:
A) All the vessels, glassware, tubing parts, and valves are cleaned and dried before assembly.
B) Regenerate the semi-preparative HPLC column 62 by eluting the column inversely with 180 mL of 80% methanol aqueous solution.
C) The hot cell surface area is cleaned with 70% alcohol.
D) Turn on the power for the module 10 and other equipment.
E) Turn on and set the heater controller 14 for the oil bath 22 (front panel; 40 volt input) for 115° C.; check the oil bath temperature with a digital thermometer.
F) After re-equilibrating the HPLC column 62 with 200 mL of the mobile phase, check the semi-prep HPLC system. Measure the pump flow rate by collecting mobile phase via the 'collection line' in a 10 mL gradual cylinder at 5 mL/min for 2 min. Note the pressure at that flow rate, then lower the flow rate to 1 mL/min and switch V2 to 'waste'.
G) Rinse the alumina cartridge 54 with 6 mL of anhydrous MeCN with a 6 mL syringe. H) Cool the 0.1 M NH$_4$OAc/0.02 M L-ascorbic acid solution in refrigerator.
I) Activate the MP-1 anion resin cartridge 42 by washing with 12 mL of 1M KHCO$_3$ solution followed by 2×12 mL of 18MΩ water.
J) Insert the activated MP-1 resin cartridge 42 in the pinch valve (V1) loop and place the fluoride trap into the Capintec well 45.
K) Add Kryptofix®/MeCN solution (1 mL, plastic syringe) to the reaction vessel 44.
L) The product vial 84 with two sterile filters (one for filtration 86 and one for venting 88) is ordered from Cyclotron and assembled by Cyclotron staff in sterile environment.
M) Label pre-assembled 30 mL sterile product vial 84 with label '18FDDNP HSA/saline/EtOH' and batch number 'MM-DD-YY'.
N) Add stirring bar 74 and 9 mL 18 MΩ water into the HPLC fraction dilution vessel 68.
O) Assemble the module 10, leaving the ten (10) PTFE tubing terminals hanging out on the door of the hot cell.
P) Add 2.5 mL of saline to the open mixing vessel 80 with a 6 mL plastic syringe.
Q) Fill the HPLC injection loop 24 with HPLC mobile phase via line 5.

A number of solutions are prepared prior to the reaction process. This includes: (1) Kryptofix®/MeCN solution (10 mg/mL); (2) KHCO$_3$ solution (1M); (3) K$_2$CO$_3$ solution (0.25% weight:volume basis); (4) NH$_4$OAc/L-ascorbic acid solution (0.1 M/0.02 M); (5) HPLC mobile phase (MeCN/0.1 M NH$_4$OAc+0.02 M L-ascorbic acid).

[F-18]Fluorination Reaction:
(1) Delivery of [F-18]fluoride ion solution (typically 1 to 5 Ci based on cyclotron production capabilities) to the reaction vessel 44:
  a. Note down the radioactivity (& time) of [F-18]fluoride ion trapped on anion resin cartridge 42 using readout 12.
  b. Turn on valve V1 (depress the electrical switch on the hot cell panel).
  c. Release the [F-18]fluoride ion to the reaction vessel 44, pre-loaded with 1 mL of Kryptofix® solution, by passing 0.4 mL of 0.25% K$_2$CO$_3$ solution followed by 0.1 mL 18 MΩ water through the resin cartridge via Line 1.
  d. Turn off V1 (elevate the electrical switch on the hot cell panel).
  e. Note down the radioactivity (& time) of [F-18]fluoride ion residue in using readout 12.
  f. Open the side door of the hot cell and quickly remove the F-18 delivery line from the reaction vessel.
(2) Drying [F-18]fluoride/Kryptofix® complex:
  a. Introduce a gentle stream of nitrogen to the [F-18] fluoride ion solution via line 3 by adjusting the nitrogen flow rate with a metering valve.
  b. Raise the jack that holds to oil bath 22 to immerse the reaction vessel 44 in the oil bath 22 heated to 115° C.
  c. When the ground glass joint at the top of the reaction vessel 44 appears partially dry (~5-6 min), add 0.5 mL of anhydrous acetonitrile via line 2 to the reaction vessel 44 and continue with nitrogen bubbling.
  d. Repeat twice more the azeotropic evaporation with anhydrous acetonitrile with 0.5 mL each time. At this point, the ground glass joint of the reaction vessel 44 should appear completely dry (~15 min in total).
  e. Decrease the temperature of the oil bath 22 from 115° C. to 93° C. during the last two evaporations of acetonitrile.
(3) [F-18]Fluorination reaction:
  a. Lower the oil bath 22 and add precursor DDNPTs (2.2-2.5 mg) in anhydrous acetonitrile (0.7 mL) with a 1 mL glass syringe via line 2 to the dried [F-18]fluoride ion/Kryptofix® complex residue in reaction vessel. Details regarding the synthesis of DDNPTs may be found in Liu et al., High-Yield, Automated Radiosynthesis of 2-(1-{6-[(2-[18F]Fluoroethyl)(methyl)amino]-2-naphthyl}ethylidene)malononitrite ([18F]FDDNP) Ready for Animal or Human Administration, Molecular Imaging and Biology, Vol. 9. pp. 6-16 (2007), which is incorporated by reference herein.

Mix the contents of reaction vessel by gentle bubbling of nitrogen for a few seconds.

b. Elevate the oil bath 22 to heat the reaction mixture at 90-95° C.

c. Stop heating of the reaction vessel 44 at fifteen (15) minutes time point by lowering the oil bath 22.

d. Cool the reaction mixture by bubbling nitrogen stream for 2 minutes.

Pre-Purification:

(1) Transfer the cooled reaction mixture from the reaction vessel 44 to the syringe barrel 52 by pulling vacuum with a 60 mL plastic syringe via line 3.

(2) Push with air pressure via line 3 the liquid through the alumina Sep-Pak® cartridge 54 and into the injection vessel 56.

(3) Add 0.5 mL of anhydrous MeCN to the reaction vessel 44 and repeat steps 1 and 2.

(4) Add another 0.5 mL of anhydrous MeCN to the reaction vessel 44 and repeat steps 1 and 2 again.

HPLC Purification:

(1) Set the HPLC pump 18 flow rate to 5 mL/min during the cooling, e.g. operation in ¶ [0046-47] to pump MeCN/0.1M NH$_4$OAc+0.02M L-ascorbic acid (1:1) as prep HPLC mobile phase.

(2) Add 1.5 mL of ice-cooled/chilled NH$_4$OAc/L-ascorbic acid (0.1 M/0.02M) solution (use 3 mL plastic syringe) via line 4 to the HPLC injection vessel 56.

(3) Transfer the mixture in the HPLC injection vessel 56 to the loop of HPLC injector 24 via line 60 by applying vacuum through line 5 (withdraw the syringe attached which is also used to fill the injection loop 24 with HPLC mobile phase).

(4) Inject by switching the control box outside the hot cell to "injection".

(5) Start the strip chart recorder or plotter 20 and a stopwatch.

(6) Monitor HPLC pump 18 back pressure for potential clogging.

(7) Turn on the stirring device 30 for the dilution vessel 68 containing 9 mL of 18 MΩ water.

(8) Monitor the UV and radioactive traces on the strip chart recorder/plotter 20 and collect the radioactive peak into the dilution vessel 68 (by turning on V2) at ~21 min retention time as observed on the strip chart recorder/plotter 20. Stop the collection after 1 minute and 15 second (by turning off V2).

Extraction of Drug Substance from HPLC Fraction:

(1) Continue to stir for another 1 min.

(2) Pass the mixed liquid in the dilution vessel 68 through the cartridge 76 and let the effluent go into the HPLC waste flask 64 by applying pressure via line 6. Plug the vent tubing line 7 with a stopcock, if higher pressure is needed to pass the solution through the cartridge 76.

(3) Turn on V3 and pass 12+8 mL of sterile water (use 12 mL plastic syringe) via line 8 to wash the cartridge 76. Let the eluent go into the waste 64.

(4) Dry the cartridge 76 with a nitrogen stream.

Drug Dose Preparation and Sampling for QC:

(1) Turn on 'product 3-way valve' V4 to 'collection'.

(2) Elute the cartridge 76 with 0.5 mL of EtOH (use 1 mL sterile syringe) via line 8 slowly into the mixing vessel 80 containing 2.5 mL of sterile normal saline.

(3) Gently bubble nitrogen into mixing vessel 80 via line 8.

(4) Stop the bubbling.

(5) Take ~100 μL of the 16.7% EtOH/saline solution (Sample-1) from vessel 80 for QC.

(6) Add 3 mL of 25% human serum albumin (HSA) via line 9 to the mixing vessel 80 with very gentle bubbling of nitrogen.

(7) Stop nitrogen bubbling, turn on V5 and transfer the HSA/EtOH/saline solution by applying vacuum via line 10 to the HSA Syringe barrel 96.

(8) Turn off V5 and apply pressure via line 10 to push the product through the sterile filter 86 into the sterile product vial 84.

(9) Add another 1 mL of 25% human serum albumin and 3 mL of sterile normal saline via line 9 to the residue in mixing vessel 80.

(10) Turn on V5 and transfer the rinsing HSA by applying vacuum via line 10 to the syringe barrel 96.

(11) Turn off V5 and apply pressure via line 10 to transfer HSA through the sterile filter 86 into the product vial 84.

(12) Check filter integrity.

(13) Take 0.3 mL sample of the drug product (Sample-2) for bacterial endotoxin and sterility QC tests Power Down (1) Turn off the power for the whole module 10 inside the hot cell. Turn off the HPLC pump 18 around 25 min time point. Turn off the power strip 20 for the instruments outside of the hot cell.

The radiochemical yield (%) that is produced using this method is high; generally above 35% as seen below in Table 1. The radiochemical yield is calculated from the radioactivity of the product corrected to EOB÷Radioactivity delivered to the reaction vessel 44 corrected to EOB×100.

TABLE 1

Typical radiochemical yields of finally formulated [F-18]FDDNP with the method described herein

| Starting [F-18]⁻ activity (mCi corrected to EOB) | [F-18]FDDNP Yield (mCi corrected to EOB) | Radiochemical Yield (%) |
|---|---|---|
| 1138.5 | 440.9 | 38.7 |
| 1125.3 | 480.8 | 42.7 |
| 1242.6 | 457.0 | 36.8 |
| 1078.7 | 426.6 | 39.5 |
| 1133.4 | 529.1 | 46.7 |
| 1016.6 | 440.4 | 43.3 |
| 1160.6 | 486.3 | 41.2 |

EOB = End of bombardment for the cyclotron production of [F-18]fluoride ion.

Figure 3A:
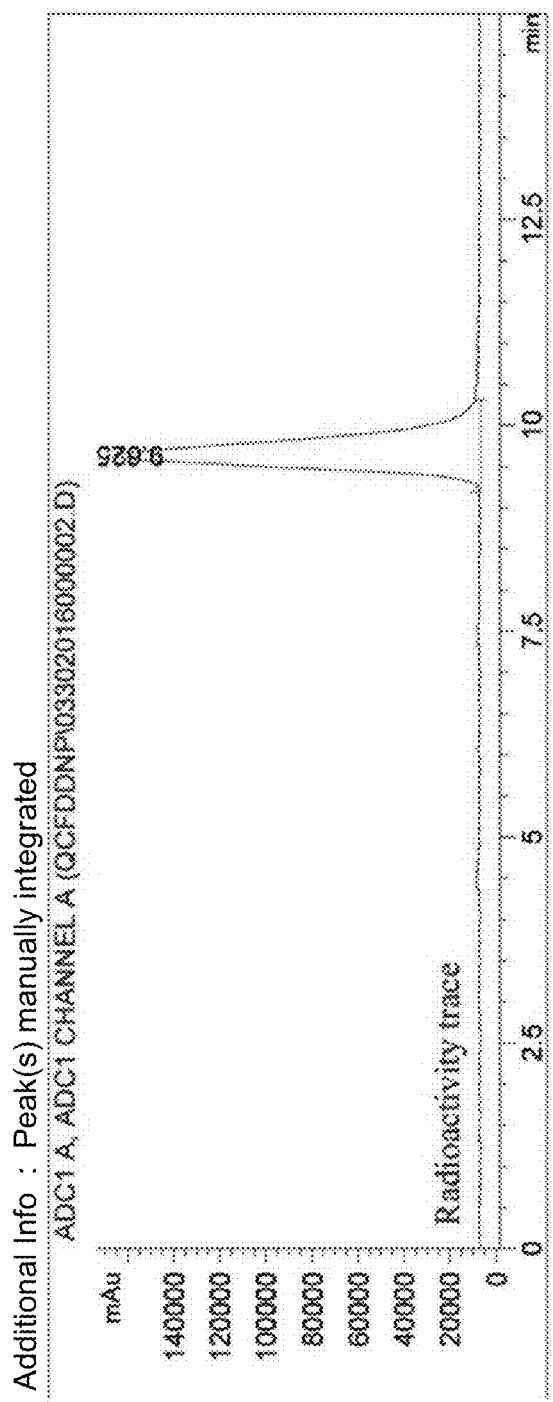
FIG. 3A illustrates the radiation trace illustrating the elution of [F-18]FDDNP from a separate analytical HPLC column. Note that the elution of [F-18]FDDNP is done using a quality control setup that utilizes a different HPLC column as well as different mobile phase conditions which causes the elution at around 9.5 minutes which is much sooner than the elution time through the semi-preparative HPLC column.
Figure 3B:
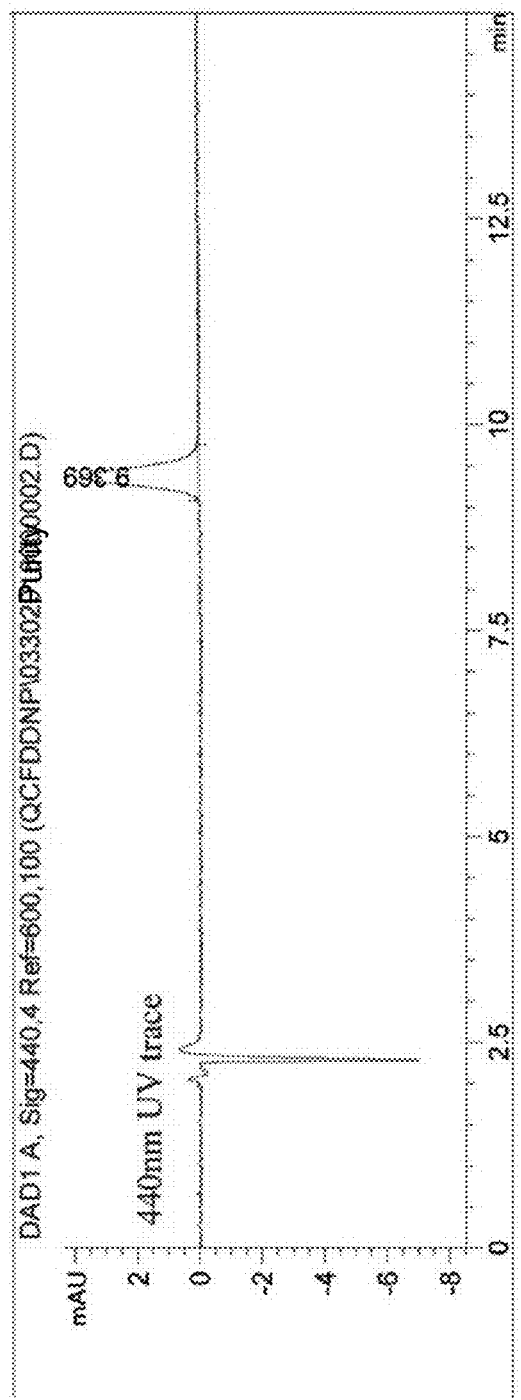
FIG. 3B illustrates the ultra-violet (UV) light absorption trace illustrating the elution of [F-18]FDDNP from the HPLC column of FIG. 3A.

FIG. 3A illustrates the radiation trace illustrating the elution of [F-18]FDDNP from a separate analytical HPLC column. Note that the elution of [F-18]FDDNP is done using a quality control setup using a different HPLC column (i.e., an analytical column) as well as different mobile phase conditions which causes the elution at around 9.5 minutes. FIG. 3B illustrates the ultra-violet (UV) light absorption trace illustrating the elution of [F-18]FDDNP from the HPLC column of FIG. 3A. For quality control purposes, radio thin layer chromatography (TLC) and gas chromatography tests may also be performed.

There are several important advantages of the method of manufacturing [F-18]FDDNP disclosed herein. First, the method does not incorporate a combination of hazardous organic solvents. Prior methods of synthesis required the use of dichloromethane (DCM), methanol (MeOH), and tetrahydrofuran (THF). See e.g., Liu et al. (2007), discussed supra. These organic solvents are classified as FDA Class 2 solvents and, under current FDA regulations and guidance, should be limited in pharmaceutical products because of their inherent toxicity. For example, the FDA has issued guidance for industry Q3C Impurities: Residual Solvents, which makes recommendations as to what amounts of residual solvent are considered safe in pharmaceuticals. See Q3C Tables and List Guidance for Industry, U.S. Department of Health and Human Services, Food and Drug Administration, Revision 3, June 2017, which is incorporated by reference herein. Solvents such as DCM and THF are not desirable to include in pharmaceutical products. For example, DCM is a known carcinogen. THF is a peroxide forming compound that is a known irritant to body tissues. Thus, in one embodiment, the manufacturing process is substantially free of organic solvents such as DCM, MeOH, or THF. The final product as described is ready for human administration under existing FDA regulations and guidance since the final product contains only a trace amount of acetonitrile (0-50 ppm) which is well below FDA established guideline limits (410 ppm). While the final product may contain some ethanol, the amount of ethanol is diluted for human administration to bring the concentration well below FDA guideline limits. Another benefit of the current method of manufacturing is the final product can be produced in less elapsed time (e.g., 100 minutes total as compared to 120 minutes). This is enabled by using a single alumina cartridge (i.e., Sep-Pak®) to substitute for the prior synthesis method that used 1% HCl aqueous solution to quench the reaction followed by C-18 Sep-Pak® extraction with an organic solvent and subsequent evaporation of the eluent. See e.g., Liu et al. (2007), discussed supra. Importantly, this is a non-aqueous workup that uses a single alumina cartridge directly after the fluorination reaction for pre-purification. This plays a significant role in reducing the autoradiolysis of [F-18]FDDNP in addition to shortening synthesis time. Thus, the method can produce a final product in less than 120 minutes in some embodiments and, more preferably, produce a final product in 100 minutes or less. For example, in one embodiment, the final product may be produced in about 90 to 100 minutes. This is significant because rapid radioactive decay that begins to occur as soon as the radioactive fluorine isotope is created (the half-life of fluorine-18 is 110 minutes). Another advantage is the high yields that are achieved using the method described herein. Generally, final product yields (when measured at the final, formulated product) range between about 30% to about 40%. However, yields higher than this have been obtained with the highest yields being around 45-46%. The method described herein is highly reliable and can produce up to one hundred (100) 10 mCi batch doses of pure, high specific activity (typically from 1 to 5 Ci/micromole) [F-18]FDDNP biomarker ready for human injection using available biomedical cyclotrons routinely producing up to 5-10 Ci of [F-18]fluoride ion.

While embodiments of the present invention have been shown and described, various modifications may be made without departing from the scope of the present invention. The invention, therefore, should not be limited, except to the following claims, and their equivalents.

What is claimed is:

1. A ready for injection product comprising 2-(1-{6-[(2-[F-18]fluoroethyl)(methyl)amino]-2-naphthyl}ethylidene)-malononitrile ([F-18]FDDNP) that is substantially free of acetonitrile formed by the process of:
    trapping [F-18]fluoride ion in a resin cartridge;
    eluting the [F-18]fluoride ion into a reaction vessel having a cryptand solution contained therein by passing a potassium salt solution followed by water through the resin cartridge, wherein a [F-18]fluoride/cryptand complex is formed therein;
    subjecting the [F-18]fluoride/cryptand complex to multiple rounds of azeotropic evaporation with anhydrous acetonitrile to form dried [F-18]fluoride ion/cryptand complex residue in the reaction vessel;
    reacting the dried [F-18]fluoride ion/cryptand complex with tosyloxy precursor 2-{[6-(2,2-dicyano-1-methyl-vinyl)-2-naphthyl](methyl)amino}ethyl-4-methylbenzenesulfonate (DDNPTs) in anhydrous acetonitrile to form a reaction product;
    passing the reaction product through an alumina cartridge and into an injection vessel;
    injecting the reaction product contained in the injection vessel to an HPLC column;
    collecting a fraction containing [F-18]FDDNP from the HPLC column in a dilution vessel;
    diluting the collected [F-18]FDDNP contained in the dilution vessel with water; and
    wherein the final product contains trace amounts of acetonitrile (0-50 ppm) at a concentration below FDA established guidelines (410 ppm).

2. The product of claim 1, wherein the final product is contained in a sterile vial.

3. The product of claim 2, wherein the final product is filtered with a filter prior to being disposed in the sterile vial.

4. The product of claim 3, wherein the final product residue is rinsed through the filter with saline and human serum albumin into the sterile vial.

5. The product of claim 2, wherein the [F-18]FDDNP in the sterile vial has a radiochemical yield of greater than 35%.

6. The product of claim 2, wherein the [F-18]FDDNP in the sterile vial is produced in more than 400 mCi (corrected to EOB) amounts with a radiochemical yield of greater than 35% with one Ci of F-18 fluoride as starting cyclotron produced activity.

7. The product of claim 1, wherein passing the reaction product directly through the alumina cartridge and into an injection vessel further comprises rinsing the reaction vessel with anhydrous acetonitrile and flowing the rinse through the alumina cartridge.

8. The product of claim 1, further comprising adding chilled ammonium acetate ($NH_4OAc$)/L-ascorbic acid to the injection vessel after passing the reaction product through an alumina cartridge and into an injection vessel.

9. The product of claim 1, wherein the HPLC column is prepared with MeCN/ammonium acetate ($NH_4OAc$) and L-ascorbic acid.

10. The product of claim 1, wherein the final product is produced in less than 120 minutes.

11. The product of claim 1, wherein the final product is produced in about 100 minutes or less.

12. The product of claim 1, wherein the [F-18]FDDNP is produced using an automated synthesizer.

13. The product of claim 1, wherein the [F-18]FDDNP is produced using at least some manual operations.

14. The product of claim 1, wherein the final product is free of methanol, dichloromethane, and/or tetrahydrofuran.

* * * * *